United States Patent [19]

Stütz et al.

[11] Patent Number: 4,939,148
[45] Date of Patent: Jul. 3, 1990

[54] AMINE DERIVATIVES, PROCESSES FOR THEIR PRODUCTION AND THEIR USE

[75] Inventors: Anton Stütz, Vienna; Peter Nussbaumer, Maria Enzersdorf, both of Austria

[73] Assignee: Sandoz, Ltd., Basel, Switzerland

[21] Appl. No.: 8,198

[22] Filed: Jan. 29, 1987

[30] Foreign Application Priority Data

Jan. 29, 1986 [DE] Fed. Rep. of Germany ....... 3602579
Mar. 19, 1986 [DE] Fed. Rep. of Germany ....... 3609123
May 26, 1986 [DE] Fed. Rep. of Germany ....... 3617635
May 26, 1986 [DE] Fed. Rep. of Germany ....... 3617637

[51] Int. Cl.$^5$ ...................... A61K 31/135; C07C 87/28
[52] U.S. Cl. ..................................... 514/649; 514/655; 564/387
[58] Field of Search ........................... 564/387; 71/121; 514/649, 658

[56] References Cited

FOREIGN PATENT DOCUMENTS 0164697 12/1985 European Pat. Off. ............ 564/387

Primary Examiner—Robert V. Hines
Attorney, Agent, or Firm—Gerald D. Sharkin; Robert S. Honor; Thomas O. McGovern

[57] ABSTRACT

Compounds of formula I

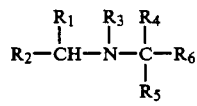

wherein
$R_1$ represents a group of formula

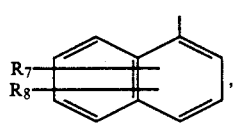

IIa

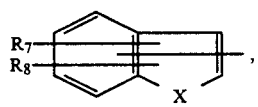

IIb

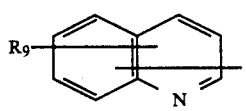

IIc

-continued

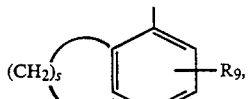

IId

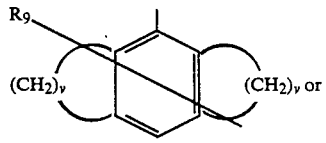

IIe

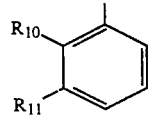

IIf and
$R_2$ represents hydrogen or lower alkyl, or
$R_1$ and $R_2$ together with the carbon atom to which they are attached represent a group of formula IIg

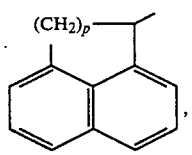
IIg $R_4$ and $R_5$ represent independently hydrogen or lower alkyl,
$R_3$ represents hydrogen, alkyl, cycloalkyl or halogenalkyl and
$R_6$ represents a group of formula

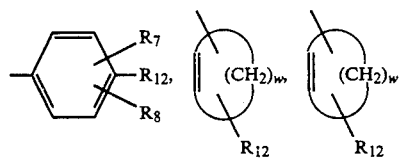

IIIa   IIIb   IIIc

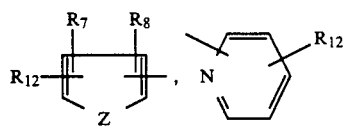

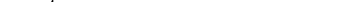

IIId   IIIe $R_1$ represents a group of formula IIa to IIf as defined above,
$R_2$ and $R_3$ together form a —(CH$_2$)—$_u$ group wherein u stands for a whole number from 1 to 8 and $R_4$, $R_5$ and $R_6$ have the meanings given above.

which compounds are indicated for use as pharmaceuticals and agrochemicals.

9 Claims, No Drawings

AMINE DERIVATIVES, PROCESSES FOR THEIR PRODUCTION AND THEIR USE

The present invention concerns the use of amine derivatives as antimycotics and agro fungicides as well as certain amine derivatives as such, pharmaceutical and agrochemical compositions containing them and processes for their production.

In particular the invention concerns the use of compounds of formula I as antimycotics and agro fungicides $$R_2-\overset{R_1}{\underset{}{C}}H-\overset{R_3}{\underset{}{N}}-\overset{R_4}{\underset{R_5}{C}}-R_6 \qquad I$$

wherein
$R_1$ represents a group of formula

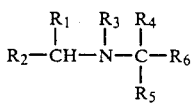

IIa

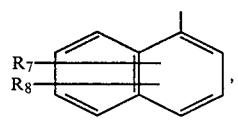

IIb

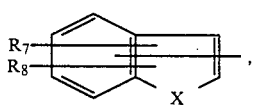

IIc

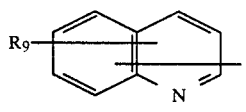

IId

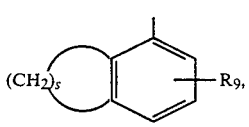

IIe

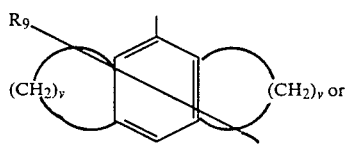

IIf and
$R_2$ represents hydrogen or lower alkyl, or
$R_1$ and $R_2$ together with the carbon atom to which they are attached represent a group of formula IIg

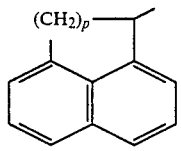

IIg whereby in formulae IIa to IIg
$R_7$ and $R_8$ represent independently hydrogen, halogen, trifluoromethyl, lower alkyl or lower alkoxy,
$R_9$ represents hydrogen, halogen, lower alkyl or lower alkoxy,
$R_{10}$ and $R_{11}$ represent independently hydrogen, halogen, trifluoromethyl, lower alkyl, lower alkoxy or lower alkylthio, whereby when one of $R_{10}$ and $R_{11}$ represents hydrogen, halogen or lower alkoxy the other is other than hydrogen,
X represents oxygen, sulphur, imino, lower alkylimino, —O—CH$_2$— or —CH$_2$—,
p stands for 1, 2 or 3,
s stands for 3, 4 or 5,
v stands for 3, 4, 5 or 6
whereby one or two of the —CH$_2$— groups in formula IId may be replaced by oxygen or sulphur,
$R_4$ and $R_5$ represent independently hydrogen or lower alkyl,
$R_3$ represents hydrogen, alkyl, cycloalkyl or halogenalkyl and
$R_6$ represents a group of formula

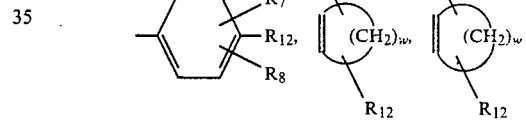

IIIa    IIIb    IIIc

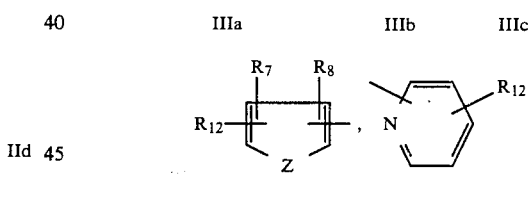

IIId    IIIe whereby in the formulae IIIa to IIIe
$R_7$ and $R_8$ have the meanings given above,
w stands for 2,3,4,5 or 6,
Z represents oxygen, sulphur or NR$_3$ wherein $R_3$ has the meaning given above and
$R_{12}$ represents alkyl, alkenyl, alkynyl, cycloalkyl, cycloalkylalkyl, lower alkoxy, lower alkoxycarbonyl, lower alkylthio, phenyl, phenalkyl, trialkylsilyl, dialkylphenylsilyl or halogen, whereby alkyl, alkenyl, alkynyl, cycloalkyl, cycloalkylalkyl, phenyl or phenalkyl may be substituted by phenyl, lower alkoxy, lower alkylthio, phenalkoxy, lower alkoxyphenyl, lower alkylphenyl, halogenphenyl, halogen or an optionally substituted heterocycle; optionally interrupted by carbonyl; or
$R_1$ represents a group of formula IIa to IIf as defined above,
$R_2$ and $R_3$ together form a —(CH$_2$)—$_u$ group wherein u stands for a whole number from 1 to 8 and $R_4$, $R_5$ and R₆ have the meanings given above, in free form or in pharmaceutically acceptable acid addition salt form.

Each lower alkyl moiety preferably contains 1 to 4, especially 2 or 1 carbon atoms. Alkyl moieties contain in particular 1 to 12, especially 2 to 8, more particularly 2 to 6 and preferably 2to 4 carbon atoms. Each alkenyl or alkynyl contains in particular 3 to 6, especially 3 or 4 carbon atoms e.g. allyl, propenyl or propynyl. Such groups as mentioned above can be straight chained or branched. A preferred cycloalkylidene is cyclohexylidene. Cycloalkyl is to be understood as embracing polycycles such as bornyl or adamantyl but is preferably cyclohexyl, cyclopentyl or cyclopropyl. Conveniently $R_7$, $R_8$ and $R_9$ are independently hydrogen or halogen. X is conveniently sulphur, imino or lower alkylimino.

Examples of heterocycles are saturated or unsaturated 5 or 6 membered rings containing one or more heteroatoms selected from nitrogen, oxygen or sulphur—e.g. thiophene. These can contain one or more substituents such as defined for $R_7$.

$R_1$ is preferably a group of formula IIc or IId in particular IIa or IIb. $R_2$ is preferably hydrogen and $R_3$ conveniently lower alkyl. $R_6$ is preferably IIIa Values for p, s, u, v and w are conveniently chosen such that seven- or preferably six- or five-membered rings are formed. Halogen stands for fluorine, chlorine or bromine.

The compounds of the present invention may be prepared by (a) reacting a compound of formula IV

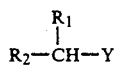     IV with a compound of formula V

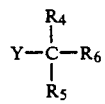     V (b) for preparing a compound of formula Ia

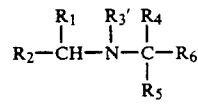     Ia introducing a R'₃ group into a compound of formula Ib

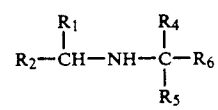     Ib (c)(i) for preparing a compound of formula Ic

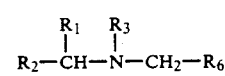     Ic reacting a compound of formula VI

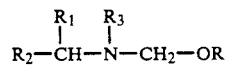     VI with a compound of formula VII

     VII or (ii) for preparing a compound of formula Id

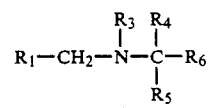     Id reacting a compound of formula VIa

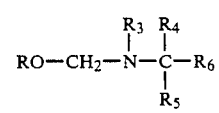     VIa with a compound of formula VIIa

     VIIa (d) for preparing a compound of formula Ie

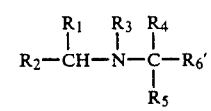     Ie reacting a compound of formula VIb

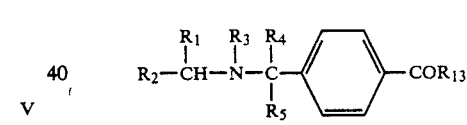     VIb with a Wittig reagent of formula IVb or IVc

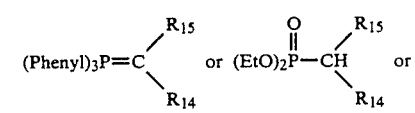

(e) for preparing a compound of formula If and Ig

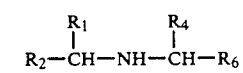     If and

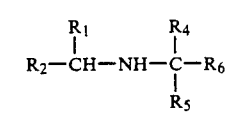     Ig reducing a Schiff's base of formula Ih, Ii

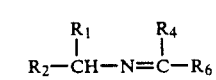     Ih or

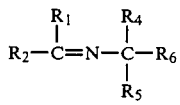 Ii whereby in the above formulae R, R$_2$, R$_3$, R$_4$, R$_5$ and R$_6$ are as defined for formula I, one Y represents a leaving group and the other —NH—R$_3$, R'$_3$ represents cycloalkyl, halogenalkyl or lower alkyl, R represents lower alkyl, Me represents a metal equivalent, R'$_6$ represents a group of formula IIIf

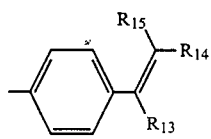 IIIf wherein R$_{13}$, R$_{14}$ and R$_{15}$ represent independently hydrogen, lower alkyl, lower alkoxy, phenyl, phenalkoxy, lower alkoxyphenyl, lower alkylphenyl, halogenphenyl, halogen or an optionally substituted heterocycle, and recovering the compound obtained in free form or acid addition salt form.

Process (a) is carried out in a manner conventional for the preparation of tertiary amines by condensation. The process can be carried out in an inert solvent such as a lower alkanol e.g. ethanol, optionally mixed with water, an aromatic hydrocarbon e.g. benzene or toluene, a cyclic ether e.g. dioxane, or a carboxylic acid dialkylamide e.g. dimethylformamide. The reaction temperature conveniently lies between room temperature and the boiling point of the reaction mixture, preferably room temperature. The process is conveniently carried out in the presence of an acid binding agent e.g. an alkali metal carbonate such as sodium carbonate. The leaving group is conveniently iodine or preferably bromine or chlorine or an organic sulphonyloxy with 1 to 10 carbon atoms e.g. an alkylsulphonyloxy, preferably with 1 to 4 carbon atoms such as mesyloxy or an alkylphenylsulphonyloxy, preferably with 7 to 10 carbon atoms such as tosyloxy.

Process (b) is carried out in a manner conventional for the alkylation of secondary amines e.g. by direct alkylation with an alkylating agent e.g. with a halogenide or a sulphate or by reductive alkylation, especially by reaction with a suitable aldehyde and subsequent or simultaneous reduction. Reductive alkylation can conveniently be carried out by reacting a compound of formula Ib in an inert solvent e.g. in a lower alkanol such as methanol, with a corresponding aldehyde. Reduction can be carried out for example with a complex metal hydride such as NaBH$_4$ or NaCNBH$_3$ as reducing agent. It can also be carried out using aqueous NaH$_2$PO$_3$-solution (H. Loibner et.al. Tetrahedron Letters 1984/2535) or formic acid which can serve simultaneously as reducing agent and reaction medium.

Process (c) can be carried out in a manner conventional for reactions involving organometal compounds. It is preferably carried out in an inert solvent e.g. in an ether between −20° C. and +50° C.

Process (d) can be carried out in a manner conventional for Wittig reactions preferably in an aprotic solvent such as a cyclic ether e.g. tetrahydrofuran or an aromatic hydrocarbon e.g. toluene between 20° C. and the boiling point of the reaction mixture.

Reduction according to process (e) can be carried out for example with a complex hydride such as NaBH$_4$. It is preferably carried out in an inert solvent e.g. in a lower alkanol such as methanol at room temperature.

The final products can be isolated and purified in conventional manner. Free bases of the compounds of formula I can be converted into salt forms and vice versa. Suitable acid addition salts are the hydrochloride, hydrogen fumarate or naphthalin-1,5-disulphonate.

The starting materials of formulae VI and VIa can be prepared by reaction of the corresponding amine of formula IV or V with formaldehyde and a lower alcohol of formula ROH.

The compounds of formula Ih can be prepared by reaction of a compound of formula IVd

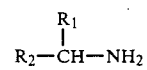 IVd with a compound of formula VIII

 VIII wherein R$_1$, R$_2$, R$_4$ and R$_6$ are as defined above.

Starting materials of formula Ii can be prepared by reacting a compound of formula IVe

 IVe with a compound of formula IX

 IX

The remaining intermediates are either known or can be prepared analogously to known processes or e.g. as described in the examples.

Some of compounds of formula I are new and also form part of the invention.

These are the compounds of formula Ij

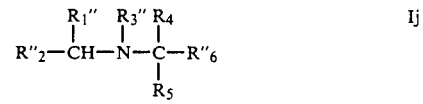 Ij wherein R$_4$ and R$_5$ are as defined above and R''$_1$, R''$_2$, R''$_3$ and R''$_6$ have the same meanings as R$_1$, R$_2$, R$_3$ and R$_6$ respectively with the proviso that (a) when R''$_1$ stands for naphthyl, R''$_2$, R''$_3$, R$_4$ and R$_5$ stand for hydrogen and R''$_6$ stands for a group IIIa wherein R$_8$ is hydrogen then R$_{12}$ and R$_7$ are not both halogen and R$_{12}$ is not halogen or methyl when R$_7$ is hydrogen.

(b) when R''$_1$ stands for a group

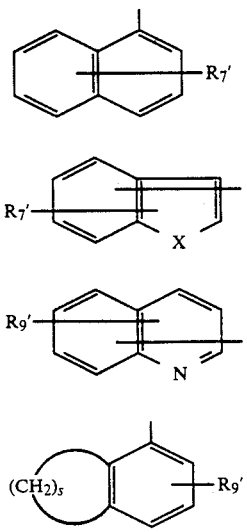

wherein R'₇ and R'₉ represent independently hydrogen, lower alkyl, lower alkoxy or halogen and s stands for 3, 4 or 5, R"₂ represents hydrogen or lower alkyl, X represents oxygen, sulphur or nitrogen and R₄ and R₅ represent hydrogen then R"₆ does not stand for a group

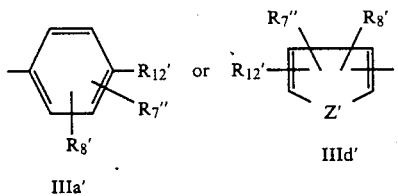

wherein Z' represents oxygen or sulphur, R"₇ represents hydrogen, R'₈ represents hydrogen, halogen or lower alkyl and R'₁₂ represents hydrogen, alkyl, cycloalkyl, halogenalkyl or alkyl; in free form or in acid addition salt form.

A preferred group of compounds for use as antimycotics and agro fungicides are those of formula Ij as defined above.

A further preferred group of compounds of formula I are those wherein (a) R₁ represents a group of formula IIa to IIf and R₂ represents hydrogen or lower alkyl or R₁ and R₂ together represent a group of formula IIg whereby in the formulae IIa to IIg R₇ and R₈ represent independently hydrogen, halogen, trifluoromethyl, lower alkyl or lower alkoxy and R₉ represents hydrogen, halogen, lower alkyl or lower alkoxy, R₁₀ and R₁₁ represent independently hydrogen, lower alkyl, halogen, trifluoromethyl, lower alkoxy or lower alkylthio, whereby when one of R₁₀ or R₁₁ represents hydrogen, halogen or lower alkoxy the other is not hydrogen, X represents oxygen, sulphur, imino, lower alkylamino or —CH₂—, p stands for 1, 2, or 3, u stands for 3, 4 or 5 and v stands for 3, 4, 5 or 6 and in the group of formula IId one or two of the CH₂ groups may be replaced by oxygen or sulphur, R₄ and R₅ represent independently hydrogen or lower alkyl, R₃ represents hydrogen, cycloalkyl, halogenalkyl or alkyl and R₆ represents a group of formula IIIa to IIIe, whereby R₇ and R₈ are as hereindefined, w stands for 2, 3, 4, 5 or 6, z stands for oxygen, sulphur or N—R₃ wherein R₃ is as herein defined and R₁₂ represents alkyl, alkenyl, alkynyl, cycloalkylalkyl, lower alkoxy, lower alkylthio, phenyl, phenalkyl, trialkylsilyl, dialkylphenylsilyl or halogen, whereby alkyl, alkenyl, alkynyl, cycloalkylalkyl, phenyl and phenalkyl can be substituted by lower alkoxy; optionally interrupted by carbonyl or (b) R₁ represents a group of formula IIa to IIf as defined under (a), R₂ and R₃ represent together —(CH₂)ᵤ— whereby u stands for a whole number from 1 to 8 and R₄, R₅ and R₆ are as herein defined.

A further preferred group of compounds of formula I are those wherein (a) R₁ represents a group of formula IIa or IIb (b) R₂ represents hydrogen or lower alkyl in particular hydrogen, (c) R₃ represents hydrogen or alkyl in particular lower alkyl and (d) R₆ represents a group of formula IIIa whereby R₇ and R₈ represent independently, hydrogen, halogen or lower alkoxy in particular hydrogen, X represents —O—CH₂—, oxygen or sulphur in particular sulphur, R₄ and R₅ represent independently hydrogen or lower alkyl in particular hydrogen and R₁₂ represents alkyl, alkenyl, alkynyl, cycloalkylalkyl, lower alkoxy, lower alkoxycarbonyl, lower alkylthio, phenyl, phenalkyl, trialkylsilyl, dialkylphenylsilyl or halogen whereby alkyl, alkenyl, alkynyl, cycloalkylalkyl, phenyl or phenylalkyl can be substituted by phenyl, lower alkoxy, lower alkylthio, phenalkoxy, lower alkoxyphenyl, lower alkylphenyl, halogenphenyl, halogen or an optionally substituted heterocycle; optionally interrupted by carbonyl.

A further preferred group of compounds of formula I are those wherein R₁ represents a group of formula IIa, IIb, IIc, IId or IIe and R₂ represent hydrogen or lower alkyl or R₁ and R₂ together represent a group of formula IIg whereby R₇ and R₈ represent independently hydrogen, halogen, trifluoromethyl, lower alkyl, lower alkoxy and R₉ represents hydrogen, halogen, lower alkyl or lower alkoxy, R₁₀ and R₁₁ represent independently hydrogen, lower alkyl, halogen, trifluoromethyl, lower alkoxy or lower alkylthio whereby when one of R₁₀ or R₁₁ is hydrogen, halogen or lower alkoxy the other is not hydrogen, X represents oxygen, sulphur, imino, lower alkylimino, —O—CH₂— or —CH₂—, p stands for 1, 2 or 3, s stands for 3, 4 or 6 and v stands for 3, 4, 5 or 6 and one or two CH₂ groups in formula IId may be replaced by oxygen or sulphur, R₄ and R₅ represent independently hydrogen or lower alkyl, R₃ represents hydrogen, cycloalkyl, halogenalkyl or alkyl and R₆ represents a group of formula IIIa, IIIb, IIIc, IIId or IIIe, whereby R₇ and R₈ are as herein defined, w stands for 2, 3, 4, 5 or 6, Z stands for oxygen, sulphur or N—R₃ wherein R₃ is as defined above and R₁₂ is as defined under formula I or R₁ represents a group of formula IIa to IIe, R₂ and R₃ together represent —(CH₂)ᵤ— wherein u is a whole number from 1 to 8 and R₄, R₅ and R₆ are as defined above.

The compounds of formula I possess advantageous chemotherapeutical properties and in particular exhibit on local or oral application an antimycotic activity and are thus indicated for use as pharmaceuticals in particular as antimycotics. This activity can be established on various families and species of mycetes e.g. Trichophyton spp., Aspergillus spp., Microsporum spp., *Sporothrix schenckii* and Candida spp. both in vitro dilution tests at concentrations of from 0.003 to 50 ug/ml and in vivo in the experimental skin mycosis test on guinea pigs and in intravaginal-intrauterine or disseminated infections. In the skin mycosis model the test substance is taken up in polyethyleneglycol and rubbed daily for 7 days on the infected skin surface. The antimycotic activity could be observed at concentrations of 0.1 to 2%. The oral activity can be demonstrated in vivo in the guinea pig trichophytosis model in a dosage range of ca. 2 to 70 mg/kg of body weight.

For the above-mentioned use, the dose administered will, of course, vary depending on the compound employed, mode of administration and treatment desired. However, in general, satisfactory results are obtained when administered at a daily dosage of from 1 to 30 mg/kg of animal body weight, conveniently given in divided doses two to four times daily, or in controlled release form. For larger mammals having an approximate body weight of 70 kg the corresponding daily dosage is for example in the range of from 70 to 2000 mg; dosage forms suitable for e.g. oral administration comprise from 17.5 to 1000 mg of active ingredient.

The compounds of the invention may be administered in similar manner to known standards for use in such indications.

A suitable daily dosage will depend on a number of factors such as relative potency of activity. It has for example been determined in the experimental skin mycosis model that the preferred compound according to the invention N-Methyl-N-(1-naphthylmethyl)-4-(2-phenyl-2-propyl)benzylamine exhibited a curative dosage (i.e. dosage at which all guinea pigs infected with Trichlophyton mentagrophytes var. quinckeanum 158 are mycologically cured) of 9×6 mg/kg in Miglyol compared with 9×60 mg/kg for Griseofulvin.

It is therefore indicated that the compounds be administered at similar or lower dosages than conventionally employed for Griseofulvin.

The compounds of the invention may be employed in the free base form or in the form of pharmaceutically acceptable acid addition salts. In general these forms exhibit the same order of activity as the free base forms. Examples of such acid addition salts include the hydrochloride, hydrogen fumarate and naphthaline-1,5-disulfonate.

The compounds may be admixed with conventional pharmaceutically acceptable diluents and carriers, and, optionally other excipients and administered orally, topically, i.v. or parenterally in such forms as tablets, capsules, creams, tinctures or injectable preparations.

Such compositions also form part of the invention.

The invention also concerns a method of combatting infections and diseases caused by mycetes comprising administering to a subject in need of such treatment an effective amount of a compound of formula I in free base form or in the form of a pharmaceutically acceptable salt thereof and such compounds for use as pharmaceuticals, in particular as anti-mycotic agents.

The compounds of the invention in free form or in agriculturally acceptable salt or metal complex form are also suitable for combatting phytopathogenic fungi. This fungicidal activity can be demonstrated i.a. in in vivo tests against Uromyces appendiculatus (bean rust) on runner beans as well as against other rust fungi (e.g. Hemileia, Puccinia), on coffee, wheat, flax and ornamentals (e.g. pelargonium, snapdragon); and against Erysiphe cichoracearum on cucumber as well as against other powdery mildews (e.g. E. Graminis f. sp. tritici, E. gram. f. sp. hordei, Podosphaera leucotricha, Uncinula recator) on wheat, barley, apple and vines.

The following examples illustrate the invention. All temperatures are given in degrees centigrade.

EXAMPLE 1

N-(5,7-difluoro-1-naphthylmethyl)-N-methyl-4-tert.butylbenzylamine (process a)

To a mixture of 0.3 g of N-methyl-4-tert.butylbenzylamine, 0.25 g of potassium carbonate and 5 ml of abs. dimethylformamide (DMF) are added dropwise 0.4 g of 5,7-difluoro-1-bromomethylnaphthalene and the mixture stirred overnight at RT. The solvent is removed under vacuum and the residue partitioned between ether and water. The organic phase is dried and evaporated. The pure product is obtained as an oil following chromatography on silica gel (eluant:hexane/ethylacetate=95/5).

EXAMPLE 2

N-(4-tert.butyl-1-cyclohexenylmethyl)-1-naphthylmethylamine (process e)

2 g of 4-tert.Butyl-1-cyclohexenecarbaldehyde, 1.9 g of 1-naphthylmethylamine and 15 ml of toluene are warmed at 70° for 4 hours with a 4 Å molecular sieve. The mixture is filtered, washed through with ether and the filtrate evaporated. The residue is dissolved in 30 ml of absolute methanol and reacted within ½ hours with two portions each of 0.5 g of sodium borohydride. The mixture is stirred for 2 hours at room temperature, evaporated and the residue partitioned between water and dichloromethane. The organic phase is dissolved in a little methanol and reacted with an excess of methanolic hydrochloric acid and evaporated to dryness. The residue is recrystallized from isopropanol/ether. By treatment with 1N caustic soda and extraction with ether the title compound is obtained as pure base as an oil, m.p. (hydrochloride):153°–155°.

EXAMPLE 3

N-(4-tert.butyl-1-cyclohexenylmethyl)-N-(1-naphthylmethyl)methylamine (process b)

0.8 g of N-(4-tert.butyl-1-cyclohexenylmethyl)-1-naphthylmethylamine are reacted with 13 ml of 1N NaH$_2$PO$_3$-solution and brought into solution by the addition of 15 ml of dioxane. Following addition of 1.1 ml 37% formaline solution the mixture is warmed to 60° for ½ hour, made alkaline with caustic soda and extracted with ether. Following drying and evaporation of the organic phase the pure product is obtained as an oil.

EXAMPLE 4

N-Methyl-N-(1-naphthylmethyl)-4-(2-phenyl-2-propyl)benzylamine (process c)

A Grignard reagent is prepared from 3 g of 2-(4-bromophenyl)-2-phenylpropane and 265 mg of magnesium in 25 ml of ether. 2.5 g of N-ethoxymethyl-N-methyl-1-naphthylmethylamine in 5 ml of ether are added dropwise at room temperature with vigorous stirring and the mixture then refluxed for 4 hours. Following addition of sat. aq. ammonium chloride and stirring for ½ hour the aqueous phase is extracted with ether. The combined organic phases are dried and the solvent distilled off. By column chromatography on silica gel (eluant:toluene/ethyl acetate=95/5) the pure product is obtained as an oil.

EXAMPLE 5

N-Methyl-N-(1-naphthylmethyl)-4-[1-(4-methoxyphenyl))-ethenyl]benzylamine (process d)

1.37 g of Methyltriphenylphosphonium bromide/sodium amide are stirred for 15 minutes at room temperature in 5 ml of toluene. 1 g of N-methyl-N-(1-naphthylmethyl)-4-(4-methoxybenzoyl)benzylamine are added and the mixture refluxed for 1½ hours. Following concentration the residue is taken up in ether, filtered and the filtrate concentrated and chromatographed over silica gel with toluene. The title compound is obtained as an oil.

Analogously to Examples 1 to 5 or as otherwise hereinbefore described, the following compounds of formula Ik are obtained

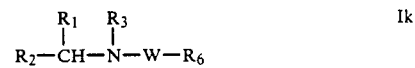

| Ex: | R₁ | R₂ | R₃ | W | R₆ | |
|---|---|---|---|---|---|---|
| 6 | 1-naphthyl | H | CH₃ | —CH₂— | —C₆H₄—C≡C.C(CH₃)₃ | Oil |
| 7 | " | H | CH₃ | " | —C₆H₄—C₆H₅ (biphenyl) | Oil |
| 8 | " | H | CH₃ | " | 2,4,6-trimethylphenyl | Oil |
| 9 | " | (piperidine, R₂-R₃ together) | | " | —C₆H₄—C(CH₃)₃ | Oil |
| 10 | 2,3-methylenedioxyphenyl | H | CH₃ | " | " | Oil |
| 11 | 1-naphthyl | H | CH₃ | " | —C₆H₄—Si(CH₃)₃ | Oil |
| 12 | " | H | CH₃ | " | —C₆H₄—C(cyclopropyl)(C₆H₅) | Oil |
| 13 | acenaphthyl (R₁-R₂ together) | | H | " | —C₆H₄—C(CH₃)₃ | m.p. 68–72° |
| 14 | " | " | CH₃ | " | " | Oil |

-continued

| Ex: | R₁ | R₂ | R₃ | W | R₆ | |
|---|---|---|---|---|---|---|
| 15 | naphthyl (1-methyl) | H | CH₃ | −CH(CH₃)− | " | Oil |
| 16 | naphthyl (1-methyl) | H | CH₃ | −CH₂− | 4-(2-phenylethenyl)phenyl | m.p. 90–95° |
| 17 | 4-(CH₃)₃C-phenyl | H | CH₃ | " | 4-C(CH₃)₃-phenyl | Oil |
| 18 | naphthyl (1-methyl) | H | cyclopropyl | " | " | Oil |
| 19 | 5,8-difluoro-1-methylnaphthyl | H | CH₃ | " | " | Oil |
| 20 | naphthyl (1-methyl) | H | CH₃ | " | 4-O.C(CH₃)₃-phenyl | m.p. 88.5° |
| 21 | " | H | −CH₂CH₂F | " | 4-C(CH₃)₃-phenyl | Oil |
| 22 | 4-methyl-indacenyl | H | CH₃ | " | " | Oil |
| 23 | naphthyl (1-methyl) | H | CH₃ | " | 2-methyl-4-(C≡C-C(CH₃)₃)-phenyl | Oil |
| 24 | " | H | CH₃ | " | 4-[Si(CH₃)₂-phenyl]phenyl | Oil |
| 25 | " | H | CH₃ | " | 4-[C(CH₃)₂-OCH₃]phenyl | Oil |

-continued

| Ex: | R₁ | R₂ | R₃ | W | R₆ | |
|---|---|---|---|---|---|---|
| 26 | " | H | CH₃ | " | —C₆H₄—COOCH₃ | Oil |
| 27 | " | H | CH₃ | " | —C₆H₄—CO.C(CH₃)₃ | Oil |
| 28 | naphthyl | H | CH₃ | —CH₂— | —C₆H₄—CO—C₆H₄—OCH₃ | Oil |
| 29 | " | H | CH₃ | " | —C₆H₄—CO—C₆H₄—CH₃ | Oil |
| 30 | " | H | CH₃ | " | —C₆H₄—C(=CH₂)—C₆H₄—CH₃ | Oil |
| 31 | " | H | CH₃ | " | —C₆H₄—C(=CH₂)—C₆H₅ | Oil |
| 32 | " | H | CH₃ | " | —C₆H₄—CO—(2-thienyl-5-Cl) | Oil |
| 33 | " | H | CH₃ | " | —C₆H₄—C(=CH₂)—(2-thienyl-5-Cl) | Oil |
| 34 | " | H | CH₃ | " | —C₆H₄—C(cyclopropyl)—C₆H₄—Cl | Oil |
| 35 | " | H | CH₃ | " | —C₆H₄—C(CH₃)₂—C₆H₄—CH₃ | Oil |
| 36 | " | H | CH₃ | " | —C₆H₄—C(CH₃)₃ | Oil, m.p. (HCl): 205–207° |
| 37 | " | H | CH₃ | " | —C₆H₄—C(C₂H₅)₃ | Oil |

-continued

| Ex: | R₁ | R₂ | R₃ | W | R₆ | |
|---|---|---|---|---|---|---|
| 38 | naphthyl | H | CH₃ | —CH₂— | 4-CH₃-phenyl | Oil |
| 39 | " | H | CH₃ | " | 4-Br-phenyl | Oil |
| 40 | " | H | CH₃ | " | 4-J-phenyl | Oil |
| 41 | 3-chloro-benzothiophene | H | CH₃ | " | 4-C(CH₃)₃-phenyl | Oil |
| 42 | naphthyl | H | C₂H₅ | " | " | Oil, m.p.(HCl): 182–184° |
| 43 | " | H | CH₃ | " | 4-CF₃-phenyl | Oil |
| 44 | 4-OCH₃-naphthyl | H | CH₃ | " | 4-C(CH₃)₃-phenyl | Oil |
| 45 | benzothiophen-2-yl | H | CH₃ | " | " | Oil |
| 46 | benzothiophen-3-yl | H | CH₃ | " | " | Oil |
| 47 | 3-bromo-benzothiophene | H | CH₃ | " | " | Oil |
| 48 | naphthyl | H | H | " | 4-CH(CH₃)₂-phenyl | Oil |
| 49 | " | H | CH₃ | " | " | Oil |

-continued

| Ex: | R₁ | R₂ | R₃ | W | R₆ | |
|---|---|---|---|---|---|---|
| 50 | naphthyl (1-methyl) | H | CH₃ | —CH₂— | 4-C(CH₃)(C₂H₅)(CH₃)-phenyl | Oil, m.p.(HCl): 169–171° |
| 51 | 2-methyl-3-bromobenzofuran | H | CH₃ | " | 4-C(CH₃)₃-phenyl | Oil |
| 52 | naphthyl (1-methyl) | H | CH₃ | " | 4-C(CH₃)₃-phenyl | Oil |
| 53 | 4-fluoro-naphthyl (1-methyl) | H | CH₃ | " | 4-C(CH₃)₃-phenyl | Oil, m.p.(HCl): 210–214° |
| 54 | 2-methyl-2H-chromene | H | CH₃ | " | " | Oil |
| 55 | naphthyl (1-methyl) | H | H | " | 4-(CH₂)₃CH₃-phenyl | Oil |
| 56 | " | H | CH₃ | " | " | Oil |
| 57 | " | H | H | " | 4-C(CH₃)₃-phenyl | Oil |
| 58 | 6-fluoro-naphthyl (1-methyl) | H | CH₃ | " | " | Oil |
| 59 | 5,7-difluoro-naphthyl (1-methyl) | H | CH₃ | " | 4-C(CH₃)(phenyl)(CH₃)-phenyl | Oil |
| 60 | 2,3-dimethylphenyl | H | CH₃ | " | 4-C(CH₃)₃-phenyl | Oil |
| 61 | " | H | CH₃ | " | 4-C(CH₃)(phenyl)-phenyl | Oil |

-continued
| Ex: | R₁ | R₂ | R₃ | W | R₆ | |
|---|---|---|---|---|---|---|
| 62 | 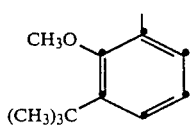 | H | CH₃ | " | 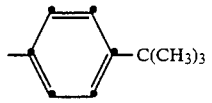 | Oil |
| 63 | 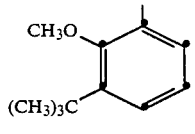 | H | CH₃ | —CH₂— | 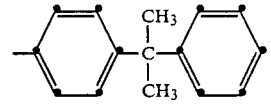 | Oil |
| 64 | 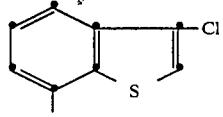 | H | CH₃ | " | " | Oil |
| 65 | 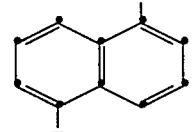 | H | CH₃ | " | " | Oil, m.p.(HCl): 186–189° |
| 66 | 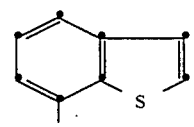 | H | CH₃ | " | " | Oil |
| 67 | 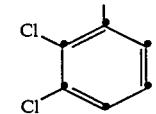 | H | CH₃ | " | " | Oil |
| 68 | " | H | CH₃ | " | 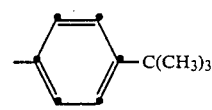 | Oil |
| 69 | 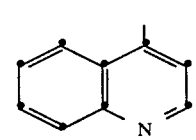 | H | CH₃ | " | " | Oil |
| 70 | 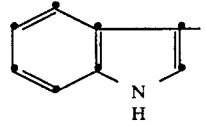 | H | CH₃ | " | " | Oil |
| 71 | 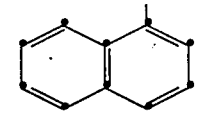 | H | CH₃ | " | 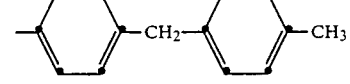 | Oil |
| 72 | " | H | CH₃ | " | 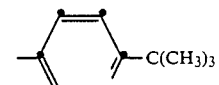 | Oil |

The required starting materials can be prepared e.g. as follows:

(A) 4-(3,3-Dimethyl-1-butynyl)benzylbromide (for Example 6)

3.35 g of 4-(3,3-Dimethyl-1-butynyl)toluene, 3.47 g of N-bromosuccinimide and 100 mg of dibenzoylperoxide in 50 ml of carbon tetrachloride are refluxed for 8 hours. The mixture is filtered and the solvent removed under vacuum. The pure product is obtained as an oil following chromatography over silica gel using hexane as an eluant.

Analogously to (A) the following compounds can be obtained as oils:

(B) 4-Bromomethyl-4'-methylbenzophenone (for example 29)

(C) 2-(4-Bromomethylphenyl)-2-(4-toluene) propane (for Example 35)

(D) 3-tert.Butylbenzylbromide (for Example 17 and 52)

(E) 2-(3,3-dimethyl-1-butylnyl)benzylbromide (for Example 23)

(F) 4-(2-Methoxy-2-propyl)benzylbromide (for Example 25)

(G) 3-(Bromomethyl)-6-tert.butylpyridine (for Example 72)

(H) N-Methyl-4-phenylbenzylamine (for Example 7)

10 g of 4-Biphenylcarbaldehyde and 40 ml of 33% ethanolic methylamine are stirred overnight at room temperature with a 4 Å molecular sieve. The mixture is filtered and concentrated under vacuum. The residue is treated in 60 ml of ethanol with 2 g of sodium borohydride and stirred for 3 hours. The solvent is removed under vacuum, the residue partitioned between ether and water and the organic phase dried and concentrated. The pure base is obtained as an oil following chromatography on silica gel with dichloromethane/ethanol=9/1 as eluant.

Analogously to (H) the following compounds can be obtained as oils:

(I) N-(2,3-Methylenedioxybenzyl)methylamine (for Example 10)

(J) N-(1-Naphthylmethyl)cyclopropylamine (for Example 18)

(K) N-Methyl-2,3-dimethylbenzylamine (for Examples 60 and 61)

(L) N-Ethoxymethyl-N-methyl-1-naphthylmethylamine (for Examples 4, 37, 50 and 71)

21 g of N-methyl-1-naphthylmethylamine and 9 g of abs. ethanol are treated under ice-cooling in portions with 3.6 g of paraformaldehyde and the mixture stirred for 1 hour at room temperature. The reaction mixture is treated with dichloromethane, filtered and concentrated. The pure product is obtained as a pale yellow oil following vacuum distillation (1.3 mbar/135°-138°).

(M) N-(5,7Difluoro-1-naphthylmethyl)methylamine (for Examples 1 and 59)

(a) 4-(2,4-Difluorophenyl)-4-one-butyric acid. 11.4 g of 1,3-Difluorobenzene and 28 g of aluminiumchloride are taken up in 75 ml of dichloromethane and treated at 38° with 10 g of succinic anhydride in small portions and then refluxed for 6 hours. The mixture is poured onto ice/hydrochloric acid, treated with dichloromethane and stirred for ½ hour. The phases are separated, the aqueous phase extracted with dichloromethane and the combined organic phases shaken with dilute caustic soda. The aqueous alkaline solution is washed with ether and made acidic with hydrochloric acid. The precipitate is filtered off under suction, washed with water and dried (m.p. 113°-115°).

(b) 4-(2,4-Difluorophenyl)butyric acid. 50 g of Zinc, 5 g of mercury (II) chloride, 2.5 ml of conc. hydrochloric acid and 75 ml of water are thoroughly stirred for 10 minutes. The liquid is decanted off and the amalgamated zinc treated with 30 ml of water, 75 ml of conc. hydrochloric acid, 3 ml of acetic acid and 16 g of 4-(2,4-difluorophenyl)-4-one-butyric acid. The mixture is refluxed for 8 hours whereby 10 ml of conc. hydrochloric acid are added every 2 hours. The organic phase is removed, the solution decanted from the zinc, extracted with toluene and the combined organic phases washed with water, dried and concentrated. The residue is dissolved in excess 1N caustic soda, treated with 200 mg of palladium on active charcoal and hydrogenated for 36 hours at room temperature and normal pressure. The mixture is filtered, made acidic and extracted with ether. The crystalline crude product can be purified by ball-tube distillation at 0.13 mbar/120°, m.p. 45°-47°.

(c) 5,7-Difluoro-1-tetralone. 120 g of Polyphosphoric acid and 12 g of phosphorous pentoxide are stirred to homogeneity at 60°. 43 g of 4-(2,4-Difluorophenyl)-butyric acid are added and the mixture stirred for 1½ hours at 80°, poured onto ice-water and extracted with ether. The combined organic phases are washed with sodium carbonate solution and sodium chloride solution, dried, stirred with a little active charcoal and evaporated. The crude product can be purified by silica gel chromatography (eluant:hexane/ethylacetate=4/1) or vacuum sublimation at 0.65 mbar/100°, m.p. 89°-91°.

(d) 5,7-Difluoro-1-methyl-1-tetralol. 2 g of 5,7-Difluoro-1-tetralone are dissolved in 20 ml of ether and added to a Grignard reagent prepared from 0.34 g of magnesium and 2 g of methyliodide in ether. After refluxing for 2½ hours the mixture is poured onto ice-/sat. ammonium chloride and stirred ½ hour. The aqueous phase is extracted with ether and purified to a colourless oil by column chromatography over silica gel (eluant:toluene/ethylacetate=9/1).

(e) 5,7-Difluoro-1-methylnaphthalene. 2.5 g of 5,7-Difluoro-1-methyl-tetralol, 3.6 g of triphenylmethanol and 2.6 g of trifluoroacetic acid anhydride are refluxed for 5 hours in 16 ml of trifluoroacetic acid. The mixture is poured onto ice-water and extracted with dichloromethane. The organic phase is washed neutral with sodium bicarbonate solution, dried and concentrated. The oily crude product can be purified by chromatography over silica gel (eluant:hexane).

(f) 5,7-Difluoro-1-bromomethylnaphthaline. 1.35 g of 5,7-Difluoro-1-methylnaphthaline in 10 ml of carbon tetrachloride are refluxed for 4½ hours with 1.4 g of N-bromosuccinimide and 50 mg of dibenzoylperoxide. The cooled mixture is filtered and the solvent removed under vacuum. The purity of the crystalline crude product is sufficient for further reaction, m.p. 74°-76.5°.

(g) N-(5,7-Difluoro-1-naphthylmethyl)methylamine. 2.3 g of 5,7-Difluoro-1-bromomethylnaphthaline are dissolved in 10 ml of ethanol and slowly added dropwise with cooling to 15 ml of a 35% ethanolic methylamino solution. After 1 hour cooling is discontinued and the mixture stirred overnight at room temperature. The solvent is removed under vacuum, the residue taken up in 2N hydrochlorid acid, the aqueous phase washed with ether and made alkaline with solid potassium carbonate. By extraction with ether the title compound is obtained as a colourless oil, m.p. (HCl): 224°-228°.

(N) 5,8-Difluoro-1-bromomethylnaphthaline (for Example 19)

(a) 5,8-Difluoro-4-methyl-1-tetralol. 5 g of 5,8-Difluoro-4-methyl-1-tetralone are dissolved in 75 ml of methanol and treated in small portions with 1 g of sodium borohydride. After 2 hours at room temperature the mixture is concentrated and the residue partitioned between water and ether. The aqueous phase is extracted with ether and the combined organic phases dried and concentrated. Recrystallisation from n-hexane yields the pure product as colourless crystals, m.p. 73°-75°.

(b) 5,8-Difluoro-1-methylnaphthaline. 3 g of 5,8-Difluoro-4-methyl-1-tetralol are refluxed for 5 hours with 1 g of sulphur. The cold mixture is diluted with ether, filtered and the solvent removed at 0°. The product is purified by column chromatography over silica gel (eluant:hexane).

(c) 5,8-Dichloro-1-bromomethylnaphthaline. Analogous to (If) to obtain the pure compound following chromatography over silica gel (eluant:hexane/ethylacetate=98/2).

(O) (5-Fluoro-1-naphthylmethy)methylamine (for Examples 53 and 65)

(a) 5-Fluoro-1-naphthaldehyde. 1.95 g of 5-Fluoro-1-naphthonitrile are dissolved in 40 ml of abs. toluene and cooled to −30°. At this temperature 11 ml of diisobutylaluminiumhydride (20% in toluene) are added dropwise and stirring continued for 2 hours without cooling. The phases are separated, the aqueous solution extracted with toluene and the combined organic phases dried and concentrated. The pure product is obtained as colourless crystals upon recrystallisation from ether/petroleum ether, m.p. 93°.

(b) (5-Fluoro-1-naphthylmethyl)methylamine. The compound is obtained from 5-fluoro-1-naphthaldehyde and methylamine analogously to Example 2 as a colourless oil.

(P) 4-(Dimethylphenylsilyl)benzylbromide (for Example 24)

(a) 4-(Dimethylphenylsilyl)toluene. 5 g of Bromotoluene are dissolved in 30 ml of tetrahydrofuran and slowly treated at −65° with an equimolar amount of butyllithium in hexane. After 30 minutes at −65° 5 g of dimethylphenylchloridesilane are added dropwise and cooling discontinued. After 2 hours at room temperature the mixture is poured onto ice-water, extracted with dichloromethane and ball-tube distilled (0.13 mbar/95°).

(b) 4-(Dimethylphenylsilyl)benzylbromide. Proceeds analogously to (A) to obtain a crude product which can be reacted further without purification.

(Q) 1-Phenyl-1-(4-bromomethylphenyl)ethylene (for Example 31)

(a) 1-Methoxy-1-phenyl-1-tolylethane. 2 g of 1-Phenyl-1-tolylethanol are stirred overnight with 0.56 g of 80% NaH in 50 ml of tetrahydrofuran, 3.7 g of methyliodide added and stirring continued for 6 hours. The mixture is worked up with aq. HCl, extracted with dichloromethane and the oily product purified over a silica gel column with cyclohexane as eluant.

(b) 1-Phenyl-1-(4-bromomethylphenyl)ethylene. Proceeds analogously to (A) to obtain, starting from 1-methoxy-1-phenyl-1-tolylethane, the title compound as an oil.

(R) 5-Chloro-2-(4-bromomethylbenzoyl)thiophen (for Example 32)

(a) 5-Chloro-2-(4-methylbenzoyl)thiophen. 5.17 g of $AlCl_3$ are suspended in 1.2 ml of dichloroethane. 3.84 g of 2-Chlorothiophen and 5 g of p-toluylchloride are added dropwise with cooling. Following stirring for 1.5 hours at room temperature the mixture is worked up with aq. HCl, extracted with dichloromethane and the oily product purified on silica gel with toluene as eluant.

(b) 5-Chloro-2-(4-bromomethylbenzoyl)thiophen. Proceeds analogously to (A) to obtain, starting from 5-chloro-2-(4-methylbenzoyl)thiophen, the title compound as an oil.

(S) 1-(4-Chlorophenyl)-1-(4-aminomethylphenyl)cyclopropane (for Example 34)

(a) 1-(4-Chlorophenyl)-1-(4-cyanophenyl)ethylene. Proceeds analogously to Example 5) starting from 4-chloro-4'-cyanobenzophenone to obtain an oily product which can be directly further reacted.

(b) 1-(4-Chlorophenyl)-1-(4-cyanophenyl)cyclopropane. 600 mg of Copper powder are cauterized with 10 mg of iodine in 10 ml of toluene. 1.2 g of Diiodomethane and 500 mg of 1-(4-cyanophenyl)-1-(4-chlorophenyl)-ethylene are added and the mixture refluxed for 140 hours and then filtered and the filtrate concentrated. The oily residue is chromatographed on silica gel with toluene as eluant.

(c) 1-(4-Chlorophenyl)-1-(4-aminomethylphenyl)cyclopropane. 230 ml of Lithiumaluminiumhydride are suspended in 10 ml of tetrahydrofuran, 234 mg of 1-(4-chlorophenyl)-1-(4-cyanophenyl)cyclopropane in 5 ml tetrahydrofuran added dropwise and the mixture refluxed for 18 hours. The mixture is then hydrolysed with 1N HCl and extracted with dichloromethane. The oily title compound is directly reacted further.

(T) N-Methyl-3-tert.butyl-2-methoxybenzylamine (for Examples 62 and 63)

(a) 3-tert.Butyl-2-methoxybenzylbromide. Proceeds analogously to (A) starting from (2-tert.butyl-6-methylphenyl)methylether) as crude product suitable for further reaction.

(b) N-Methyl-3-tert.butyl-2-methoxybenzylamine. Proceeds analogously to M)g) to obtain a colourless oil.

(U) 1-Phenyl-[1-(4-aminomethyl)phenyl]cyclopropane (for Example 12)

Proceeds analogously to (S) starting from 1-phenyl-1-(4-cyanophenyl)ethylene to obtain the title compound as an oil.

| | NMR-Spectra |
|---|---|
| Ex. | Spectra |
| 1 | 7.9–8.1 (m, 1H); 7.6–7.8 (m, 1H); 7.2–7.6 (m, 6H); 6.98 (ddd, J = 10.5 + 8.5 + 2.5 Hz, 1H); 3.83 (s, 2H); 3.57 (s,2H); 2.19 (s,3H); 1.31 (s, 9H). |
| 2 | 8.0–8.25 (m, 1H); 7.65–8.0 (m, 2H); 7.30–7.65 (m, 4H); 5.55–5.80 (m, 1H); 4.18 (s, 2H); 3.26 (s, 2H); 1.55–2.30 (m, 5H); 1.50 (s, 1H); 1.0–1.4 (m, 2H); 0.87 (s, 9H). |
| 3 | 8.2–8.45 (m, 1H); 7.65–7.95 (m, 2H); 7.30–7.65 (m, 4H); 5.55–5.75 (m, 1H); 3.85 (s, 2H); 2.94 (s, 2H); 2.12 (s, 3H); 1.65–2.2 (m, 5H); 1.05–1.50 (m, 2H); 0.86 (s, 9H). |
| 4 | 8.10–8.34 (m, 1H); 7.64–7.95 (m, 2H); 7.03–7.58 (m, 13H); 3.92 (s, |

-continued
NMR-Spectra

| Ex. | Spectra |
|---|---|
| | 2H); 3.55 (s, 2H); 2.19 (s, 3H); 1.65 (s, 6H). |
| 5 | 8.20–8.44 (m, 1H); 7.75–7.85 (m, 2H); 7.37–7.58 (m, 4H); 7.23–7.36 (m, 6H); 6.82–6.87 (m, 2H); 5.34–5.38 (m, 2H); 3.95 (s, 2H); 3.81 (s, 3H); 3.60 (s, 2H); 2.21 (s, 3H). |
| 6 | 8.18–8.36 (m, 1H); 7.65–7.95 (m, 2H); 7.18–7.60 (m, 8H); 3.90 (s, 2H); 3.55 (s, 2H); 2.15 (s, 3H); 1.30 (s, 9H). |
| 7 | 8.26–8.33 (m, 1H); 7.75–7.88 (m, 2H); 7.28–7.62 (m, 13H); 3.96 (s, 2H); 3.63 (s, 2H); 2.23 (s, 3H). |
| 8 | 7.64–8.05 (m, 3H); 7.27–7.53 (m, 4H); 6.86 (s, 2H); 3.85 (s, 2H); 3.58 (s, 2H); 2.33 (s, 6H); 2.25 (s, 3H); 2.13 (s, 3H). |
| 9 | 8.20–9.00 (br, 1H); 7.10–7.95 (m, 10H); 3.75–3.95 (m, 1H); 3.77 (d, 1H, J = 13,5 Hz); 3.00–3.25 (m, 1H); 2.80 (d, 1H, J = 13,5 Hz); 1.45–2.10 (m, 7H); 1.27 (s, 9H). |
| 10 | 7.32 (s, 4H); 6.70–6.95 (m, 3H); 5.95 (s, 2H); 3.54 (s, 2H); 3.52 (s, 2H); 2.20 (s, 3H); 1.30 (s, 9H). |
| 11 | 8.15–8.40 (m, 1H); 7.68–7.95 (m, 2H); 7.25–7.65 (m, 8H); 3.94 (s, 2H); 3.60 (s, 2H); 2.20 (s, 3H); 0.24 (s, 9H). |
| 12 | 8.16–8.27 (m, 1H); 7.70–7.88 (m, 2H); 6.84–7.52 (m, 13H); 3.88 (s, 2H); 3.50 (s, 2H); 2.25 (s, 3H); 1.22–1.28 (m, 4H). |
| 13 | 7.2–7.85 (m, 10H); 4.9 (dd, J = 7.5 + 4 Hz, 1H); 3.95 (s, 2H); 3.74 (dd, J = 18 + 7.5 Hz, 1H); 3.25 (dd, J = 18 + 4 Hz, 1H); 1.7 (s, 1H); 1.30 (s, 9H). |
| 14 | 7.2–7.8 (m, 10H); 5.0 (dd, J = 7.5 + 4 Hz, 1H); 3.25–3.6 (m, 4H); 2.19 (s, 3H); 1.30 (s, 9H). |
| 15 | 8.0–8.25 (m, 1H); 7.7–8.0 (m, 2H); 7.2–7.65 (m, 8H); 3.96 (s, 2H); 3.84 (qua, J = 6.5 Hz, 1H); 2.15 (s, 3H); 1.54 (d, J = 6.5 Hz, 3H); 1.33 (s, 9H). |
| 16 | 8.15–8.45 (m, 1H); 7.65–8.0 (m, 2H); 7.15–7.65 (m, 13H); 7.1 (s, 2H); 3.95 (s, 2H); 3.6 (s, 2H); 2.2 (s, 3H). |
| 17 | 7.15–7.5 (m, 8H); 3.54 (s, 2H); 3.49 (s, 2H); 2.21 (s, 3H); 1.34 (s, 9H); 1.32 (s, 9H). |
| 18 | 7.95–8.2 (m, 1H); 7.6–7.95 (m, 2H); 7.1–7.6 (m, 8H); 4.1 (s, 2H); 3.73 (s, 2H); 1.7–2.05 (m, 1H); 1.32 (s, 9H); 0.1–0.4 (m, 4H). |
| 19 | 8.0 (d, J = 8 Hz, 1H); 7.76 (d, J = 7 Hz, 1H); 7.52 (dd, J = 8 + 7 Hz, 1H); 7.25–7.35 (AA'BB'-System, 4H); 7.0–7.13 (m, 2H); 4.11 (d, J = 3 Hz, 2H); 3.64 (s, 2H); 2.21 (s, 3H); 1.3 (s, 9H). |
| 20 | 8.05–8.27 (m, 1H); 6.75–7.90 (m, 10H); 3.90 (s, 2H); 3.53 (s, 2H); 2.18 (s, 3H); 1.30 (s, 9H). |
| 21 | 8.15–8.40 (m, 1H); 7.65–7.95 (m, 2H); 7.15–7.65 (m, 8H); 4.50 (dt, J = 48 + 5, 5 Hz, 2H); 4.12 (s, 2H); 3.70 (s, 2H); 2.84 (dt, J = 26 + 5.5 Hz, 2H); 1.29 (s, 9H). |
| 22 | 8.14–8.42 (m, 4H); 7.03 (s, 1H); 3.48 (s, 2H); 3.45 (s, 2H); 2.75–3.05 (m, 8H); 2.08 (s, 3H); 1.85–2.20 (m, 4H); 1.30 (s, 9H). |
| 23 | 8.16–8.40 (m, 1H); 7.68–7.95 (m, 2H); 7.04–7.64 (m, 7H); 3.99 (s, 2H); 3.81 (s, 2H); 2.22 (s, 3H); 1.36 (s, 9H). |
| 24 | 8.20–8.42 (m, 1H); 7.70–8.00 (m, 2H); 7.24–7.68 (m, 13H); 4.00 (s, 2H); 3.66 (s, 2H); 2.27 (s, 3H); 0.59 (s, 6H). |
| 25 | 8.12–8.40 (m, 1H); 7.66–7.95 (m, 2H); 7.20–7.62 (m, 8H); 3.95 (s, 2H); 3.60 (s, 2H); 3.07 (s, 3H); 2.22 (s, 3H); 1.53 (s, 6H). |
| 26 | 8.20–8.42 (m, 1H); 7.72–8.12 (m, 4H); 7.30–7.68 (m, 6H); 3.95 (s, 2H); 3.90 (s, 3H); 3.62 (s, 2H); 2.20 (s, 3H). |
| 27 | 8.20–8.42 (m, 1H); 7.26–7.98 (m, 10H); 3.97 (s, 2H); 3.61 (s, 2H); 2.21 (s, 3H); 1.34 (s, 9H). |
| 28 | 8.20–8.38 (m, 1H); 7.36–7.84 (m, 12H); 6.86–6.98 (m, 2H); 3.98 (s, 2H); 3.86 (s, 3H); 3.64 (s, 2H); 2.21 (s, 3H). |
| 29 | 8.27–8.39 (m, 1H); 7.24–7.94 (m, 14H); 4.00 (s, 2H); 3.66 (s, 2H); 2.44 (s, 3H); 2.24 (s, 3H). |
| 30 | 8.24–8.34 (m, 1H); 7.74–7.92 (m, 2H); 7.08–7.60 (m, 12H); 5.40 (s, 2H); 3.95 (s, 2H); 3.60 (s, 2H); 2.34 (s, 3H); 2.20 (s, 3H). |
| 31 | 8.24–8.35 (m, 1H); 7.74–7.92 (m, 2H); 7.12–7.60 (m, 13H); 5.42–5.47 (m, 2H); 3.95 (s, 2H); 3.60 (s, 2H); 2.20 (s, 3H). |
| 32 | 8.30–8.41 (m, 1H); 7.74–7.96 (m, 4H); 7.36–7.64 (m, 7H); 6.98–7.03 (d, J = 4 Hz, 1H); 4.02 (s, 2H); 3.68 (s, 2H); 2.26 (s, 3H). |
| 33 | 8.24–8.28 (m, 1H); 7.72–7.85 (m, 3H); 7.34–7.52 (m, 7H); 6.74 (d, J = 4 Hz, 1H); 6.64 (d, J = 4 Hz, 1H); 5.44 (s, 1H); 5.18 (s, 1H); 3.95 (s, 2H); 3.60 (s, 2H); 2.24 (s, 3H). |
| 34 | 8.18–8.24 (m, 1H); 7.76–7.84 (m, 2H); 7.08–7.48 (m, 12H); 3.92 (s, 2H); 3.54 (s, 2H); 2.17 (s, 3H); 1.20–1.29 (m, 4H). |
| 35 | 8.16–8.28 (m, 1H); 7.74–7.90 (m, 2H); 7.10–7.57 (m, 12H); 3.96 (s, 2H); 3.60 (s, 2H); 2.25 (s, 3H); 2.21 (s, 3H); 1.64 (s, 6H). |
| 36 | 8.13–8.35 (m, 1H); 7.64–7.92 (m, 2H); 7.24–7.60 (m, 8H); 3.92 (s, 2H); 3.57 (s, 2H); 2.20 (s, 3H); 1.30 (s, 9H). |
| 37 | 8.05–8.4 (m, 1H); 7.6–8.0 (m, 2H); 7.1–7.6 (m, 8H); 3.92 (s, 2H); 3.58 (s, 2H); 2.2 (s, 3H); 1.66 (qua, J = 7 Hz, 6H); 0.64 (t, J = 7 Hz, 9H); |
| 38 | 8.20–8.35 (m, 1H); 7.70–7.92 (m, 2H); 7.36–7.60 (m, 4H); 7.05–7.35 (m, 4H); 3.90 (s, 2H); 3.56 (s, 2H); 2.32 (s, 3H); 2.18 (s, 3H). |
| 39 | 8.20–8.36 (m, 1H); 7.70–7.95 (m, 2H); 7.15–7.62 (m, 8H); 3.93 (s, 2H); 3.52 (s, 2H); 2.18 (s, 3H). |
| 40 | 8.18–8.36 (m, 1H); 7.30–7.96 (m, 8H); 7.00–7.18 (m, 2H); 3.92 (s, |

-continued
NMR-Spectra

| Ex. | Spectra |
|---|---|
| | 2H); 3.50 (s, 2H); 2.17 (s, 3H). |
| 41 | 7.70–7.90 (m, 1H); 7.20–7.55 (m, 7H); 3.82 (s, 2H); 3.59 (s, 2H); 2.16 (s, 3H); 1.32 (s, 9H). |
| 42 | 8.18–8.40 (m, 1H); 7.16–7.90 (m, 10H); 3.99 (s, 2H); 3.58 (s, 2H); 2.56 (qua, 2H, J = 6,75 Hz); 1.28 (s, 9H); 1.10 (t, 3H, J = 6,75 Hz). |
| 43 | 8.20–8.42 (m, 1H); 7.30–8.00 (m, 10H); 3.97 (s, 2H); 3.61 (s, 2H); 2.20 (s, 3H). |
| 44 | 8.10–8.40 (m, 2H); 7.15–7.65 (m, 7H); 6.75 (d, J = 8 Hz, 1H); 3.99 (s, 3H); 3.84 (s, 2H); 3.55 (s, 2H); 2.08 (s, 3H); 1.30 (s, 9H). |
| 45 | 7.75–8.05 (m, 2H); 7.20–7.55 (m, 7H); 3.76 (s, 2H); 3.56 (s, 2H); 2.12 (s, 3H); 1.31 (s, 9H). |
| 46 | 7.65–7.90 (m, 1H); 7.20–7.55 (m, 8H); 3.82 (s, 2H); 3.60 (s, 2H); 2.18 (s, 3H); 1.31 (s, 9H). |
| 47 | 7.76 (dd, J = 7 + 3 Hz, 1H); 7.2–7.55 (m, 7H); 3.81 (s, 2H); 3.58 (s, 2H); 2.15 (s, 3H); 1.3 (s, 9H). |
| 48 | 7.95–8.2 (m, 1H); 7.65–7.95 (m, 2H); 7.10–7.6 (m, 8H); 4.23 (s, 2H); 3.88 (s, 2H); 2.9 (sept, J = 7 Hz, 1H); 1.73 (s, 1H); 1.23 (d, J = 7 Hz, 6H). |
| 49 | 8.1–8.4 (m, 1H); 7.65–8.0 (m, 2H); 7.10–7.6 (m, 8H); 3.92 (s, 2H); 3.58 (s, 2H); 2.90 (sept, J = 7 Hz, 1H); 2.2 (s, 3H); 1.24 (d, J = 7 Hz, 6H). |
| 50 | 8.1–8.35 (m, 1H); 7.7–7.95 (m, 2H); 7.25–7.65 (m, 8H); 3.95 (s, 2H); 3.6 (s, 2H); 2.2 (s, 3H); 1.64 (qua, J = 7.5 Hz, 2H); 1.26 (s, 6H); 0.66 (t, J = 7.5 Hz, 3H). |
| 51 | 7.63–7.7 (m, 1H); 7.15–7.45 (m, 7H); 3.59 (s, 2H); 3.55 (s, 2H); 2.22 (s, 3H); 1.32 (s, 9H). |
| 52 | 8.2–8.45 (m, 1H); 7.65–8.0 (m, 2H); 7.10–7.6 (m, 8H); 3.92 (s, 2H); 3.61 (s, 2H); 2.22 (s, 3H); 1.33 (s, 9H). |
| 53 | 7.9–8.15 (m, 2H); 7.0–7.6 (m, 8H); 3.9 (s, 2H); 3.56 (s, 2H); 2.19 (s, 3H); 1.3 (s, 9H). |
| 54 | 6.73–7.48 (m, 8H); 5.75–5.85 (m, 1H); 4.70–4.85 (m, 2H); 3.52 (s, 2H); 3.28 (d, J = 1,5 Hz, 2H); 2.20 (s, 3H); 1.31 (s, 9H). |
| 55 | 7.96–8.18 (m, 1H); 7.62–7.94 (m, 2H); 7.05–7.62 (m, 8H); 4.23 (s, 2H); 3.87 (s, 2H); 2.60 (tr, J = 7,5 Hz, 2H); 2.00 (s, 1H); 1.10–1.80 (m, 4H); 0.91 (tr, J = 7 Hz, 3H). |
| 56 | 8.15–8.36 (m, 1H); 7.65–7.95 (m, 2H); 7.04–7.62 (m, 8H); 3.92 (s, 2H); 3.58 (s, 2H); 2.60 (tr, J = 7,5 Hz, 2H); 2.20 (s, 3H); 1.10–1.80 (m, 4H); 0.91 (tr, J = 7 Hz, 3H). |
| 57 | 8.02–8.24 (m, 1H); 7.66–8.0 (m, 2H); 7.22–7.64 (m, 8H); 4.26 (s, 2H); 3.90 (s, 2H); 1.69 (s, 1H); 1.33 (s, 9H). |
| 58 | 8.16–8.40 (m, 1H); 7.60–7.82 (m, 1H); 7.12–7.58 (m, 8H); 3.90 (s, 2H); 3.56 (s, 2H); 2.20 (s, 3H); 1.32 (s, 9H). |
| 59 | 7.96–8.03 (m, 1H); 7.62–7.70 (m, 1H); 7.48–7.55 (m, 1H); 7.36–7.45 (m, 1H); 7.12–7.32 (m, 9H); 6.97 (ddd, J = 10,5, 8,5 and 2,5 Hz, 1H); 3.82 (s, 2H); 3.54 (s, 2H); 2.19 (s, 3H); 1.67 (s, 6H). |
| 60 | 7.00–7.45 (m, 7H); 3.52 (s, 2H); 3.50 (s, 2H); 2.27 (s, 6H); 2.13 (s, 3H); 1.31 (s, 9H). |
| 61 | 7.00–7.45 (m, 12H); 3.52 (s, 2H); 3.50 (s, 2H); 2.30 (s, 3H); 2.27 (s, 3H); 2.15 (s, 3H); 1.70 (s, 6H). |
| 62 | 6.92–7.60 (m, 7H); 3.78 (s, 3H); 3.61 (s, 2H); 3.52 (s, 2H); 2.19 (s, 3H); 1.40 (s, 9H); 1.31 (s, 9H). |
| 63 | 6.90–7.60 (m, 12H); 3.78 (s, 3H); 3.61 (s, 2H); 3.51 (s, 2H); 2.19 (s, 3H); 1.68 (s, 6H); 1.40 (s, 9H). |
| 64 | 7.74–8.02 (m, 1H); 7.12–7.45 (m, 12H); 3.79 (s, 2H); 3.56 (s, 2H); 2.15 (s, 3H; 1.66 (s, 6H). |
| 65 | 7.90–8.15 (m, 2H); 7.02–7.06 (m, 13H); 3.90 (s, 2H); 3.55 (s, 2H); 2.19 (s, 3H); 1.66 (s, 6H). |
| 66 | 7.65–7.86 (m, 1H); 7.15–7.55 (m, 13H); 3.82 (s, 2H); 3.59 (s, 2H); 2.18 (s, 3H); 1.68 (s, 6H). |
| 67 | 7.10–7.60 (m, 12H); 3.67 (s, 2H); 3.58 (s, 2H); 2.22 (s, 3H); 1.68 (s, 6H). |
| 68 | 7.46–7.56 (m, 1H); 7.25–7.40 (m, 5H); 7.14–7.24 (m, 1H); 3.66 (s, 2H); 3.58 (s, 2H); 2.22 (s, 3H); 1.31 (s, 9H). |
| 69 | 8.86 (d, J = 5 Hz, 1H); 6.08–6.20 (m, 2H); 7.65–7.73 (m, 1H); 7.46–7.56 (m, 1H); 7.25–7.40 (m, 4H); 3.93 (s, 2H); 3.62 (s, 2H); 2.25 (s, 3H); 1.32 (s, 9H). |
| 70 | 8.25 (br s, 1H); 7.70–7.77 (m, 1H); 7.05–7.40 (m, 8H); 3.73 (s, 2H); 3.53 (s, 2H); 2.22 (s, 3H); 1.32 (s, 9H). |
| 71 | 8.20–8.25 (m, 1H); 7.74–7.84 (m, 2H); 7.07–7.47 (m, 12H); 3.93 (s, 2H); 3.92 (s, 2H); 3.55 (s, 2H); 2.29 (s, 3H); 2.18 (s, 3H). |
| 72 | 8.44–8.60 (m, 1H); 8.16–8.42 (m, 1H); 7.70–7.96 (m, 2H); 7.20–7.68 (m, 6H); 3.98 (s, 2H); 3.56 (s, 2H); 2.22 (s, 3H); 1.35 (s, 9H). |
| A | 7.22–7.48 (m, 4H); 4.46 (s, 2H); 1.30 (s, 9H). |
| B | 7.10–7.80 (m, 8H); 4.48 (s, 2H); 2.26 (s, 3H). |
| C | 7.20 (s, 4H); 7.10 (s, 4H); 4.45 (s, 2H); 2.27 (s, 3H); 1.62 (s, 6H). |
| D | 7.1–7.5 (m, 4H); 4.48 (s, 2H); 1.34 (s, 9H). |
| E | 7.15–7.50 (m, 4H); 4.67 (s, 2H); 1.37 (s, 9H). |
| F | 7.40 (s, 4H); 4.52 (s, 2H); 3.09 (s, 3H); 1.63 (s, 6H). |
| G | 8.50–8.66 (m, 1H); 7.20–7.80 (m, 2H); 4.50 (s, 2H); 1.35 (s, 9H). |
| H | 7.20–7.70 (m, 9H); 3.75 (s, 2H); 2.42 (s, 3H); 1.80 (s, 1H). |

-continued

NMR-Spectra

| Ex. | Spectra |
|---|---|
| I | 6.68 (s, 3H); 5.93 (s, 2H); 3.73 (s, 2H); 2.43 (s, 3H); 1.36 (s, 1H). |
| J | 7.85–8.25 (m, 1H); 7.2–7.8 (m, 6H); 4.2 (s, 2H); 2.1 (qui, J = 5 Hz, 1H); 1.7 (s, 1H); 0.35 (d, J = 5 Hz, 4H). |
| K | 6.95–7.25 (m, 3H); 3.70 (s, 2H); 2.50 (s, 3H); 2.28 (s, 3H); 2.25 (s, 3H); 1.10 (s, 1H). |
| L | 8.05–8.35 (m, 1H); 7.15–8.0 (m, 6H); 4.15 (s, 4H); 3.48 (qua, J = 7 Hz, 2H); 2.45 (s, 3H); 1.2 (t, J = 7 Hz, 3H). |
| M | (a) 7.98 (dt, J = 9 + 6,5 Hz, 1H); 6.8–7.1 (m, 2H); 5.8–6.8 (br, 1H); 3.2–3.4 (m, 2H); 2.8 (t, J = 6,5 Hz, 2H). |
| | (b) 7.15 (dt, J = 8 + 7 Hz, 1H); 6.7–6.9 (m, 2H); 2.68 (t, J = 7 Hz, 2H); 2.38 (t, J = 7 Hz, 2H); 1.75–2.1 (m, 2H). |
| | (c) 7.57 (ddd, J = 9, 2,5 + 1,5 Hz, 1H); 7.02 (ddd, J = 9, 8 + 2,5 Hz, 1H); 2.93 (t, J = 6,5 Hz, 2H); 2.7 (t, J = 6,5 Hz, 2H); 2.0–2.3 (m, 2H). |
| | (d) 7.12 (dd, J = 9 + 2,5 Hz, 1H); 6.86 (ddd, J = 9, 8 + 2,5 Hz, 1H); 2.63–2.71 (m, 2H); 1.96 (s, 1H); 1.7–2.0 (m, 4H); 1.51 (s, 3H). |
| | (e) 7.8–8.0 (m, 1H); 7.3–7.5 (m, 2H); 6.98 (ddd, J = 10,5,9 + 2,5 Hz, 1H); 2.6 (s, 3H). |
| | (f) 7.85–8.15 (m, 1H); 7.30–7.65 (m, 3H); 6.98 (ddd, J = 10,5, 9 + 2,5 Hz, 1H); 4.80 (s, 2H). |
| | (g) 7.80–8.15 (m, 1H); 7.15–7.65 (m, 3H); 6.90 (ddd, J = 10,5, 9 + 2,5 Hz, 1H); 4.02 (s, 2H); 2.48 (s, 3H); 1.38 (s, 1H). |
| N | (a) 6.8–6.95 (m, 2H); 5.03–5.1 (m, 1H); 3.09 (sext, J = 7 Hz, 1H); 2.57 (dd, J = 7 + 3 Hz, 1H); 1.7–2.02 (m, 4H); 1.34 (dd, J = 7 + 1,5 Hz, 3H). |
| | (b) 7.8–8.1 (m, 1H); 6.8–7.6 (m, 4H); 2.8 (d, J = 7,5 Hz, 3H). |
| | (c) 7.8–8.2 (m, 1H); 6.85–7.6 (m, 4H); 5.05 (d, J = 2,5 Hz, 2H). |
| O | (a) 10.4 (d, J = 1 Hz, 1H); 9.03 (dt, J = 8.8 + 0.7 Hz, 1H); 8.41 (dqui, J = 7,5 + 0,7 Hz, 1H); 8.05 (dd, J = 7 + 1,3 Hz, 1H); 7.71 (dd, J = 7,5 + 7 Hz, 1H); 7.63 (ddd, J = 8,8, 7,8 + 5,9 Hz, 1H); 7.27 (ddd, J = 10,4, 7,8 + 1,0 Hz, 1H). |
| | (b) 8.0–8.16 (m, 1H); 7.85–8.0 (m, 1H); 7.35–7.6 (m, 3H); 7.17 (ddd, J = 10,5, 8 + 1 Hz, 1H); 4.20 (s, 2H); 2.56 (s, 3H); 1.5 (s, 1H). |
| P | (a) 7.05–7.60 (m, 9H); 2.35 (s, 3H); 0.52 (s, 6H). |
| | (b) 7.10–7.60 (m, 9H); 4.38 (s, 2H); 0.52 (s, 6H). |
| Q | (a) 7.10–7.40 (m, 9H); 3.10 (s, 3H); 2.28 (s, 3H); 1.82 (s, 3H). |
| | (b) 7.23 (s, 9H); 5.43 (s, 2H); 4.5 (s, 2H). |
| R | (a) 7.71 (d, J = 9 Hz, 2H); 7.39 (d, J = 4 Hz, 1H); 7.25 (d, J = 9 Hz, 2H); 6.95 (d, J = 4 Hz, 1H); 2.40 (s, 3H). |
| | (b) 7.30–7.90 (m, 5H); 6.97 (d, J = 4 Hz, 1H); 4.50 (s, 2H). |
| S | (a) 7.10–7.80 (m, 8H); 5.55 (s, 2H). |
| | (b) 7.15–7.70 (m, 8H); 1.30 (s, 4H). |
| | (c) 7.15–7.30 (m, 8H); 3.80 (s, 2H); 1.80 (br s, 2H); 1.25 (s, 4H). |
| T | (a) 6.90–7.50 (m, 3H); 4.60 (s, 2H); 3.93 (s, 3H); 1.40 (s, 9H). |
| | (b) 6.85–7.40 (m, 3H); 3.80 (s, 5H); 2.46 (s, 3H); 1.50 (br s, 1H); 1.39 (s, 9H). |
| U | (b) 7.00–7.50 (m, 9H); 1.32 (s, 4H). |
| | (c) 7.15–7.25 (m, 9H); 3.80 (s, 2H); 1.60 (br s, 2H); 1.25 (s, 4H). |

We claim:

1. A compound of formula I

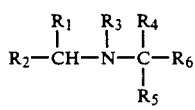

wherein

R₁ represents a group of formula

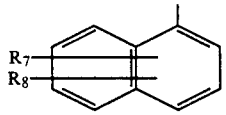

R₂ is hydrogen
R₃ is hydrogen or lower alkyl
R₄ and R₅ are both hydrogen,
R₇ and R₈ are each independently, hydrogen, halogen, trifluoromethyl, lower alkyl or lower alkoxy, and
R₆ is

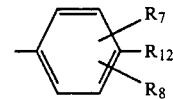

wherein
R₇ and R₈ are as defined above and
R₁₂ is alkyl substituted by phenyl, halogenphenyl, lower alkylphenyl, or lower alkoxyphenyl, in free base form or in pharmaceutically acceptable acid addition salt form.

2. The compound according to claim 1 in which R₁ is naphthyl, R₃ is methyl and R₆ is

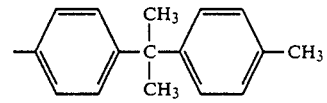

in free base form or pharmaceutically acceptable acid addition salt form.

3. The compound according to claim 1, in which $R_1$ is 5,7-difluoronaphthyl, $R_3$ is methyl and $R_6$ is

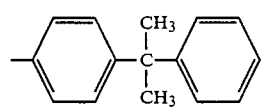

in free base form or pharmaceutically acceptable acid addition salt form

4. The compound according to claim 1 in which $R_1$ is 5-fluoronaphthyl, $R_3$ is methyl and $R_6$ is

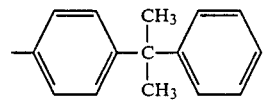

in free base form or pharmaceutically acceptable acid addition salt form.

5. The compound according to claim 1 in which $R_1$ is naphthyl, $R_3$ is methyl and $R_6$ is

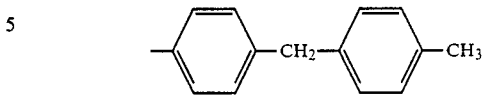

in free base form or pharmaceutically acceptable acid addition salt form.

6. N-methyl-N-(1-naphthylmethyl)-4-(2-phenyl-2-propyl)benzylamine.

7. The compound according to claim 6 in acid addition salt form.

8. A pharmaceutical composition comprising a compound of claim 1 in free form or pharmaceutically acceptable acid addition salt form and a pharmaceutically acceptable diluent or carrier therefore.

9. A method of combatting infections and diseases caused by mycetes which comprises administering to a subject in need to such treatment an effective amount of a compound of claim 1 in free form or pharmaceutically acceptable acid addition salt form.

* * * * *